US00PP17706P3

(12) United States Plant Patent
Doyle

(10) Patent No.: US PP17,706 P3
(45) Date of Patent: May 8, 2007

(54) ASIAN PEAR TREE, 85.10-23

(50) Latin Name: *Pyrus pyrifolia*
Varietal Denomination: 85.10-23

(76) Inventor: James F. Doyle, 36782 Wheeler Rd., Pleasant Hill, OR (US) 97455

( * ) Notice: Subject to any disclaimer, the term of this patent is extended or adjusted under 35 U.S.C. 154(b) by 335 days.

(21) Appl. No.: 10/970,068

(22) Filed: Oct. 20, 2004

(65) Prior Publication Data

US 2006/0085877 P1 Apr. 20, 2006

(51) Int. Cl.
*A01H 5/00* (2006.01)

(52) U.S. Cl. ..... Plt./178

(58) Field of Classification Search ..... Plt./178
See application file for complete search history.

*Primary Examiner*—Kent Bell
*Assistant Examiner*—Annette H Para
(74) *Attorney, Agent, or Firm*—Wells St. John P.S.

(57) ABSTRACT

A new and distinct variety of Asian pear tree (*Pyrus pyrifolia*) and which is denominated as 85.10-23 is described, and which produces a yellow colored white fleshed fruit which is mature for harvesting and shipment during the second and third weeks of July under the ecological conditions prevailing in the San Joaquin Valley of central California.

1 Drawing Sheet

BACKGROUND OF THE NEW VARIETY

The present invention relates to a new novel and distinct variety of Asian pear tree, *Pyrus pyrifolia,* and which has been denominated varietally as 85.10-23.

ASEXUAL REPRODUCTION—ORIGIN

The present variety of Asian pear tree is the result of a controlled hybridization made by the inventor during the spring of 1984. This hybridization took place on the inventor's property which was then located at 7685 North Thompson Avenue, Clovis, Calif.

The new variety of Asian pear tree was the result of a cross involving the Asian pear variety "Kosui" (unpatented), which was the female or seed parent, and which further was hybridized by the Asian pear variety "Yakumo" (unpatented), and which was the male or pollen parent. To accomplish this hybridization, flowers of the female parent "Kosui" were emasculated to prevent pollination by insects. Thereafter the pollen of the "Yakumo" variety was collected and physically placed on the stigmas of the emasculated "Kosui" flowers to effect cross-pollination. Seeds from this cross-pollination were later harvested at the end of the 1984 growing season. These seeds were then subsequently planted in the spring of 1985 and resulted in a group of seedlings that were given the numerical designation 85.10. This family of seedlings were observed during the 1985 and 1986 growing seasons.

At the end of the 1986 growing season, 22 seedlings were then selected for propagation onto larger, mature trees of the "Yakumo" Asian pear variety (unpatented). These trees were growing in a cultivated area in Clovis, Calif. The initial selection of seedlings was based upon the vigor of the seedling, and the vegetative characteristics. The propagation of the seedling in the existing "Yakumo" Asian pear trees also provided an opportunity for direct comparison of the fruit which were eventually borne on the seedling grafts with the fruit produced by the "Yakumo" Asian pear trees, on the same tree, and in the same geographic location.

Fruit of the present variety was observed during the 1989 growing season. The present seedling was identified as superior to others growing at that time.

The first propagation of the Asian pear variety 85.10-23 occurred during the spring of 1990. In this regard, the subsequent trees were propagated by grafting the selection onto one year old seedlings of *Pyrus betulaefolia* pear rootstock (unpatented), and which is a common rootstock used in commercial Asian pear production. Fruit was produced by these propagated trees in 1992, and significant numbers were produced in 1993 and 1994. The fruit produced by these propagated trees have been compared against the original variety and the fruit appears identical in all respects to the first fruit borne on the seedling grafts noted above.

SUMMARY OF THE VARIETY 85.10-23 is a new and distinct variety of Asian pear tree which produces fruit which is normally ripe for harvesting and shipment under the ecological conditions prevailing near Newcastle, Calif. during the second and third weeks of July. In relative comparison to the fruit produced by the "Yakumo" Asian pear tree, the present variety is distinguishable therefrom, inasmuch as the "Yakumo" variety of Asian pear tree produces relatively small and round shaped fruit. Whereas the present variety of Asian pear tree produces medium to large sized fruit which is slightly variable in fruit form from globose to somewhat turbinate in its lateral aspect. In relative comparison to the "Kosui" Asian pear tree, which produces fruit having a golden yellow to a tan skin color, the present variety is distinguishable by producing a fruit having a yellow-greenish skin which has occasional darker green mottling. In relative comparison to the "Shinsui" Asian pear tree with which the present variety is most clearly similar relative to its harvesting date, the present variety is distinguishable therefrom inasmuch as the "Shinsui" variety produces a fruit which has a russeted golden-brown skin color, and which has an ovate, small to medium sized shape. Still further, in relative comparison to the "Shinseiki" variety of Asian pear tree, which produces fruit having a similar skin color, the present variety of Asian pear tree is distinguishable therefrom inasmuch as the fruit of the "Shinseiki" Asian pear tree has a fruit shape which is flat-round, whereas the present variety has a nearly globose to somewhat turbinate shape in its lateral aspects. Moreover, the date of harvesting of the present variety of Asian pear tree 85.10-23 occurs at least two weeks before the Asian pear variety "Shinseiki" at the same geographical location.

BRIEF DESCRIPTION OF THE DRAWINGS

The accompanying drawing which is provided is a color photograph of the present Asian pear variety. The photograph depicts three whole mature fruit, additionally one fruit has been divided in half to show the flesh coloration. A vegetative shoot bearing typical leaves is also shown. The external coloration of the fruit as shown is sufficiently matured for harvesting and shipment. The colors as seen in this photograph are as nearly true as is reasonably possible in a color representation of this type. Due to chemical development, processing and printing, the leaves and fruit depicted in these photographs may or may not be accurate when compared to the actual specimen. For this reason, future color reference should be made to The Royal Horticultural Society Colour Chart 3$^{rd}$ Edition and which was published in 1995.

DETAILED DESCRIPTION

Referring more specifically to the pomological details of this new and distinct variety of Asian pear tree, the following has been observed from a thirteen year old tree of the subject variety during the 2004 growing season, and under the ecological conditions prevailing in a cultivated area which is located near Highway 193 and Fowler Road at Newcastle, Calif. All major color code designations are by reference to The Royal Horticultural Society Colour Chart 3$^{rd}$ Edition published in 1995.

Tree:

*Size.*—Average for the species.

*Vigor.*—Vigorous and hardy under typical central San Joaquin Valley climatic conditions.

*Tree form.*—Considered upright to upright spreading.

*Tree height.*—When measured at the end of the 2004 growing season, the present variety had a height of about 3.3 to about 3.4 meters. This growth included about 0.9 to about 1.4 meters of the current season's growth.

*Tree crown.*—Width — Approximately 1.5 meters. Trees of the present variety are growing in an orchard where spacing between the adjacent trees is about 1.4 meters, and the respective rows of trees are approximately 3.4 meters apart. The trees of the present variety are annually pruned into a narrow-upright vase training system. The trees of the subject invention are currently propagated on *Pyrus betulaefolia* pear rootstock (unpatented), and which is a standard pear rootstock species used for commercially propagating Asian pear trees.

*Productivity.*—Productive.

*Regularity of bearing.*—Regular.

Trunk:

*Trunk diameter.*—When measured at a distance of approximately 20 centimeters from the ground level and elevationally above the lower *Pyrus betulaefolia* rootstock, the variety has a trunk diameter of approximately 11 centimeters.

*Bark.*—Surface Texture — Moderately cracked and roughened. However, some broad smooth areas are present.

*Bark color.*—Considered medium grey (Fan #4, Sheet 197-C).

*Bark lenticels.*—Numbers — Numerous and appearing roughened on their surfaces.

*Lenticels.*—Color — Dark grey (Fan #4, Sheet 201-A).

*Lenticels.*—Shape — Considered oval.

*Lenticels.*—Size — Approximately 1.0 to about 6.0 millimeters in width, and from about 1.0 to about 3.0 millimeters in height.

Branches:

*Size.*—Considered normal in diameter for the species. The main scaffold branches of the observed tree range in diameter from about 4.0 to about 6.0 centimeters when measured at the base of the scaffold.

*Surface texture.*—Scaffold branches appear slightly smoother than the trunk surface, but have approximately the same grey color (Fan #4, Sheet 197-C).

*Lenticels.*—The lenticels seen on the branches appear to have the same development as that of the trunk, noted above.

*Upper branches.*—Size — The upper spreader branches range in size from about 1.8 to about 3.0 centimeters in diameter at their bases, while smaller hanger branches vary in thickness from about 1.1 to about 1.6 centimeters.

*Surface texture.*—Older branches — Two year old or older branches appear to have a netted surface texture, and further have numerous medium brown colored and calloused lenticels (Fan #4, Sheet 164-C).

*Older branches.*—Color — Grey-brown in color and nearly glabrous in surface texture (Fan #4, Sheet 201B).

*One year old shoots and spurs.*—Color — Considered brownish in color (Fan #4, Sheet 165-A) and having a moderately pubescent surface texture.

*Current season's shoots.*—Color — Dark brown (Fan #4, Sheet 177-A). These current season's shoots have a moderately pubescent surface texture.

*Actively growing shoots.*—Color — Light green (Fan #3, Sheet 138-A). Actively growing shoots have a highly pubescent surface texture of medium length. The pubescence appears wooly.

*Expanding shoot tips and young leaves.*—Color — Considered Orange-bronze in coloration (Fan #4, Sheet 172-C).

*Internode length.*—When measured on upright vigorous shoots, this ranges from about 4.5 to 7.5 centimeters between adjacent nodes. The length between the nodes as seen on smaller lateral shoots ranges from about 3.0 to about 5.5 centimeters, and the length between those nodes as appearing on spurs range from about 0.5 to about 1.5 centimeters.

Leaves:

*Size.*—Generally — Considered medium to large for the species. The measurements which follow have been taken from leaves growing near mid-shoot on vigorously growing current season's shoots.

*Leaf length.*—About 12.5 to about 18.9 centimeters including the leaf petiole.

*Leaf width.*—About 7.7 to about 11.6 centimeters.

*Leaf thickness.*—Considered normal for the species.

*Surface texture.*—Young immature leaves are highly pubescent on both the upper and lower leaf surfaces. As these leaves mature however, much of this pubescence is lost.

*Mature leaf texture*—Very slightly rugose. No glands are evident on the leaf.

*Leaf form.*—Generally — Considered variable from broadly lanceolate to ovate.

*Leaf apices.*—Shape — Acute and at times curled backward from the upper leaf surface. Most leaves appear somewhat folded upwards.

*Leaf surface.*—Texture — The leaf surfaces along the mid-vein are at times slightly wavy.

*Leaf color.*—Mature leaves — The upper leaf surface appears dark green (Fan #3, Sheet 137-A); and the lower surfaces are a lighter green in color (Fan #3, Sheet 138-B).

*Color.*—Mid-Vein — The primary mid-vein on the lower leaf surface is a pale yellow-green (Fan #3, Sheet 145-C).

*Leaf margins.*—Generally — Considered serrate and tipped with narrow, soft, sharp spines.

*Serrations.*—Size — Moderately large.

*Leaf margins.*—Shape — Slightly undulate.

*Leaf petiole.*—Size — Considered average and short, and further having a length of about 1.8 to about 4.5 centimeters, and a thickness of about 1.5 to 2.5 millimeters when measured at approximately mid-petiole.

*Petiole base.*—Shape — Typically considered wider and at times slightly flared, and having a thickness of about 1.5 to about 3.5 millimeters.

*Petiole.*—Color — Considered yellow-green on younger leaves (Fan #3, Sheet 144-D) and on older leaves (Fan #3, Sheet 145-C). Within the petiole groove and the petiole ridges, the color is increasingly darker (Fan #3, Sheet 138-B).

*Petiole.*—Surface texture — Lightly pubescent.

*Immature leaves.*—Surface texture — These leaves appear to have a higher degree of pubescence than mature leaves. No glands are present on the petiole.

*Leaf stipules.*—Generally — Small, thin, pale green stipules can typically be found on new growth. These leaf stipules are early deciduous.

*Leaf stipules.*—Length — About 6 to 10 millimeters on average.

*Leaf stipules.*—Width — About 0.5 to about 1.0 millimeters.

*Leaf stipules.*—Form — Considered linearly lanceolate. The leaf stipules darken and deteriorate within increasing senescence.

Flowers:

*Flower buds.*—Size — Generally considered large, plump and conic in form. The buds are considered relatively free from the bearing stem and are considered hardy under typical central San Joaquin Valley climatic conditions.

*Flower buds.*—Color — Reddish-brown (Fan #4, Sheet 175-A).

*Flower buds.*—Surface texture — Considered pubescent especially apically and over the interior side of the bud scales.

*Bloom time.*—Generally — Average to slightly late in relative comparison to other common Asian pear tree varieties growing at the same geographic location.

*Date of full bloom.*—Observed at Newcastle, Calif. on Mar. 31, 2003 and Mar. 24, 2004. In relative comparison to other known varieties, it should be understood that the date of full bloom for the Asian pear tree variety "Hosui" was Mar. 29, 2003 and Mar. 19, 2004. Still further, the date of full bloom for the parent variety "Kosui" at Newcastle, Calif. was Mar. 28, 2003 and Mar. 23, 2004.

*Duration of bloom.*—Approximately 10 days. The date and duration of bloom however, can be substantially effected by the amount of chilling hours that occur during a given year, and the geographical location where the variety is grown.

*Flower size.*—Generally — Average for the species.

*Flower diameter.*—Approximately 36 to 43 millimeters when fully expanded.

*Bloom quantity.*—Considered abundant.

*Flowers per node.*—As many as 8 can be produced.

*Flower petals.*—Size — About 18 to about 22 millimeters in length and from about 14 to about 17 millimeters in width.

*Petal numbers.*—Typically 5, but extra petals can be observed. As many as 5 extra petals can sometimes be seen. Double petalled flowers (10 petals) can be found on many fruiting branches.

*Petal form.*—Considered variable, but most frequently appears ovate.

*Petal color.*—White (Fan #4, Sheet 155-D).

*Petal claw.*—Shape — Short and truncate in form.

*Petal margins.*—Shape — Undulate.

*Petal apices.*—Form — Variable and having a somewhat pointed tip.

*Flower pedicel.*—Size — These are variable from about 21 to about 30 millimeters in length, and from about 1.0 to about 1.5 millimeters in thickness.

*Flower pedicel.*—Color — Pale green (Fan #3, Sheet 145-C).

*Flower pedicel.*—Surface Texture — Pubescent, and further having moderately sparse filamentous pubescence.

*Floral nectaries.*—Color — Yellow-brown (Fan #3, Sheet 153-B). The floral nectaries become darker with increasing senescence.

*Calyx.*—Surface Texture — Slightly pubescent.

*Calyx.*—Color — Pale green (Fan #3, Sheet 145-B).

*Sepals.*—Surface Texture — Pubescent.

*Sepals.*—Size — Relatively small and broadly lanceolate in form.

*Sepals.*—Color — Green-yellow (Fan #3, Sheet 151-B).

*Anthers.*—Size — Considered average for the species.

*Anthers.*—Color — Considered a pale rose (Fan #1, Sheet 51-B). This color appears both ventrally and dorsally.

*Pollen production.*—Considered abundant in quantity.

*Pollen.*—Color — Yellow (Fan #1, Sheet 5-A).

*Stamens.*—Size — Somewhat variable from about 5 to about 8 millimeters. The stamens are about equal in height to the tip of the pistil.

*Stamens.*—Color — White (Fan #4, Sheet 155-D).

*Pistil.*—Form — The pistil of the present variety has five styles separated to the ovary.

*Pistil*—Length — Somewhat variable from about 6 to 7 millimeters.

*Pistil.*—Surface Texture — Glabrous.

*Pistil.*—Color — Yellow-green (Fan #1, Sheet 1-D).

Fruit:

*Maturity when described.*—The fruit of the present variety of Asian pear tree is described at full commercial maturity hereinafter.

*Date of harvest.*—In 2003, the date of harvest was July 20. The date of harvest in 2002 was July 25. The date of harvesting may be effected by seasonal variations. The date of harvesting, noted above, are those that were observed at Newcastle, Calif.

*Fruit size.*—Generally — Considered medium to large in size especially for the early date of maturity. For fruit harvested from well thinned trees, the fruit diameter was about 78 to about 86 millimeters; and the fruit had a height of about 77 to about 81 millimeters.

*Fruit form.*—Generally — Slightly variable from nearly globose to somewhat turbinate when viewed in its lateral aspect. The fruit is most frequently globose or very slightly oval when viewed in transverse section.

*Fruit symmetry.*—Somewhat variable, from fully symmetrical to slightly asymmetrical or considered lopsided.

*Fruit stem.*—Size — The fruit stem has a length dimension of about 17 to about 22 millimeters; and a thickness dimension of about 2.5 to about 3 millimeters.

*Fruit stem.*—Shape — Typically, considered slightly curved.

*Fruit stem.*—Color — Light green (Fan #3, Sheet 144-B).

*Fruit stem.*—Surface Texture — Moderately pubescent.

*Fruit lenticels.*—Color — Light tan and being slightly raised and oval in form on the fruit stem surface (Fan #4, Sheet 161-A).

*Stem cavity.*—Shape — Considered uniform and acute.

*Stem cavity.*—Size — Considered moderate. The width of the stem cavity ranges from about 23 to about 28 millimeters when measured across the shoulders of the fruit. The depth of the stem cavity is variable from about 6 to about 9 millimeters.

*Fruit basin.*—Shape — Globose in form; relatively wide; and of average depth. The fruit basin sides are sloping and have what appears to be a smooth surface. Some russetting is present within the basin where the sepals were attached to the fruit. The sepals are considered deciduous.

*Fruit basin.*—Size — The fruit basin has a diameter of about 35 to about 39 millimeters; and a depth of about 13 to about 15 millimeters.

*Calyx.*—Form — The calyx opening is closed. Still further, the calyx tube is considered long and funnel shaped. Additionally, stamen remnants are often present in the calyx tube and are typically located in a marginal position.

*Core lines.*—Generally — These are distinct and clasping.

*Fruit core.*—Position — Distant and considered relatively far from the fruit stem.

*Fruit core.*—Size — Considered average in relation to the overall size of the fruit.

*Fruit carpels.*—Generally — Five carpels are present and are located within the fruit core.

*Fruit carpels.*—Shape — Obovate.

*Fruit carpel cells.*—Form — Generally speaking, these are closed in form although at times some open cells can be present.

*Fruit carpels.*—Surface Texture — The inner surface of the carpel wall is considered glabrous.

*Seeds.*—Numbers — Variable from 2 to as many as 10.

*Seeds.*—Size — Considered plump, and having a length of about 7 to about 9 millimeters; and a width from about 3 to about 5 millimeters.

*Seeds.*—Thickness — About 2 millimeters.

*Seed apex.*—Form — Acute.

*Seeds.*—Color — Dark Brown at full maturity (Fan #4, Sheet 175-A). The seeds color at full commercial maturity is a lighter tan-brown color (Fan #4, Sheet 164-B).

*Fruit skin.*—Thickness — Considered average.

*Fruit skin.*—Surface texture — Glabrous. The skin appears to tightly adhere to the underlying fruit flesh.

*Fruit skin.*—Flavor — Considered mild to neutral.

*Fruit skin.*—Color — Predominately yellow-green (Fan #3, Sheet 151-C), and occasionally, having dark green mottling (Fan #3, Sheet 144-C), which typically appears at an early stage of maturity. With advancing senescence, and at full commercial maturity, the fruit becomes a full substantially uniform yellow (Fan #1, Sheet 11-A).

*Fruit skin.*—Lenticels — Present. These are small and relatively inconspicuous.

*Fruit skin lenticel color.*—Very pale yellow (Fan #1, Sheet 1-D).

*Bloom.*—Present, and considered very thin and transparent. The bloom extends substantially over the entire skin surface.

*Fruit flesh.*—Color — White with a very slight cream-yellow tint (Fan #1, Sheet 11-D).

*Fruit flesh.*—Texture — Crisp and considered very juicy.

*Stone cells.*—Generally — Present, and average in number. The stone cells are located in the vicinity of the core area.

*Ripening.*—Considered even. The fruit holds well on the tree.

*Fruit flavor.*—Considered sweet, refreshing and mild, and having a very good commercial quality.

*Aroma.*—Considered pleasant, and slight.

*Resistance to insects and diseases.* —No particular susceptibility where noted. The present variety has not been intentionally tested to expose or detect any susceptibilities or resistance to any known plant and/or other fruit tree diseases.

Although the new variety of Asian pear tree possesses the described characteristics when grown under the ecological conditions prevailing near Newcastle, Calif., it should be understood that variations of the usual magnitude and characteristics incident to changes in growing conditions, fertilization, pruning, pest control and other horticultural management practices are to be expected.

Having thus described and illustrated my new variety of Asian pear tree, what I claim is new, and desire to secure to Plant Letters Patent is:

1. A new and distinct variety of Asian pear tree substantially as illustrated and described, and which is characterized principally as to novelty by producing an attractively colored fruit which is mature for harvesting and shipment during the second and third weeks of July under the ecological conditions prevailing in the San Joaquin Valley of central California.

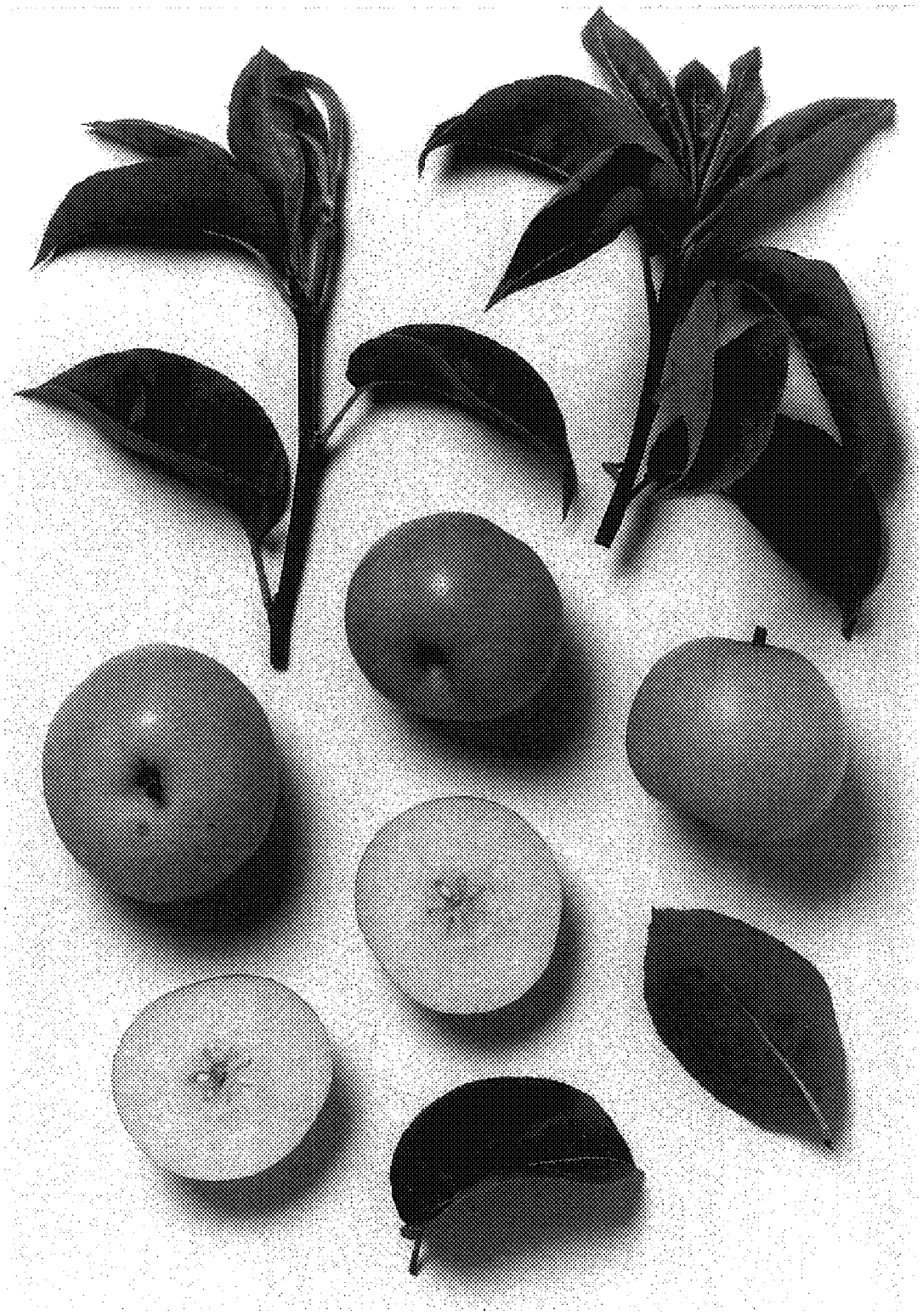

* * * * *